United States Patent [19]

Colegrove

[11] Patent Number: 5,368,862
[45] Date of Patent: Nov. 29, 1994

[54] SUSTAINED RELEASE TABLETS CONTAINING ALGINATE

[75] Inventor: George Colegrove, San Diego, Calif.

[73] Assignee: Merck & Co., Inc., Rahway, N.J.

[21] Appl. No.: 792,102

[22] Filed: Dec. 18, 1991

[51] Int. Cl.⁵ .................... A61K 9/22; A61K 47/36
[52] U.S. Cl. .................... 424/464; 424/465; 424/468; 514/779
[58] Field of Search .......... 424/464, 465, 468; 514/779; 536/3

[56] References Cited

U.S. PATENT DOCUMENTS

| | | | |
|---|---|---|---|
| 4,053,627 | 10/1977 | Sher et al. | 424/19 |
| 4,199,560 | 4/1980 | Gyarmati et al. | 424/19 |
| 4,235,966 | 11/1980 | Jarman et al. | 435/172.1 |
| 4,401,456 | 8/1983 | Connick et al. | 71/88 |
| 4,842,866 | 6/1989 | Horder et al. | 424/468 |
| 4,933,185 | 6/1990 | Wheatley et al. | 424/461 |

Primary Examiner—Thurman K. Page
Assistant Examiner—James M. Spear
Attorney, Agent, or Firm—Richard S. Parr; Melvin Winokur

[57] ABSTRACT

Sustained release tablet comprising a microbially produced alginate-type polysaccharide and an active ingredient to be delivered in controlled fashion.

6 Claims, 2 Drawing Sheets

SUSTAINED RELEASE TABLETS CONTAINING ALGINATE

BACKGROUND OF THE INVENTION

The invention relates to controlled long-acting release pharmaceutical formulations containing an active therapeutic agent and a carrier base material. More specifically, this invention relates to tablets of a controlled long-acting pharmaceutical formulation containing an active therapeutic agent and a carrier base material.

Long-acting products are widely marketed in the pharmaceutical field and are now a significant factor in the administration of a variety of active pharmaceutical agents. The advantages of such long-acting or sustained release products are well understood and a very substantial industry has developed around these products. Sustained release products permit various medications to be administered for uniform and continuous release over a prolonged period of time, thereby achieving a particular blood level of active ingredient for whatever time is thought to be advantageous to the patient. Such administration obviates the necessity of frequent administration of active ingredient and avoids the problems inherent in insuring timely and repetitive consumption of pharmaceutical product by the patient. It is possible to achieve stable blood levels of a variety of active therapeutic agents and thereby control a variety of physiological conditions. It also reduces or possibly eliminates toxic or side effects which are caused by frequent administration of active ingredients through the peaks and valleys of blood levels caused by multiple ingestion of medication.

In the production of controlled or sustained release tablets by direct compression of dry powders, a water soluble thickener is commonly used to provide a matrix for the tablet. The thickener hydrates rapidly on the surface of the tablet and swells to a gelatinous consistency through which the drug must diffuse, thus decreasing the rate of diffusion of the active drug.

Alginates derived from natural sources such as kelp, i.e. "algal alginates", are used in controlled release tablets. One of the disadvantages in using algal alginates to control release is that they are highly dependent on the pH condition of the dissolution medium. In gastric fluids, at low pH, they produce a gelled layer on the surface of the tablet which retards diffusion of the active ingredient. As pH conditions increase, however (e.g. in the intestine), algal alginates rapidly dissolve, becoming less capable of influencing drug diffusion.

The following patents describe various controlled release systems which include algal alginates.

Wheatley et al., U.S. Pat. No. 4,933,185, describes a system for controlled release of biologically active substances such as proteins. The system contains the active substance and a polysaccharide degrading enzyme encapsulated within a microcapsule. The microcapsule has an inner polysaccharide polymer core and an outer ionically interacting skin. One of the exemplary polysaccharides is alginate.

Hotder et al., U.S. Pat. No. 4,842,866, describes a controlled release system which contains an active ingredient, sodium alginate, and a calcium-sodium alginate complex. The amount of calcium used in the calcium-sodium alginate complex is precisely controlled, and the complex is self-gelling.

Connick, U.S. Pat. No. 4,401,456, describes a process for producing alginate gel beads containing an herbicide material.

Gyarmati et al., U.S. Pat. No. 4,199,560, describe solid oral pharmaceutical products with protracted active ingredient release. Tablet internal phase is composed of a hydrophobic component and a hydrophilic component.

Mitra, U.S. Pat. No. 4,163,777, describes controlled antacid delivery using polysaccharide, including sodium alginate.

Scher, U.S. Pat. No. 4,053,627, describes a method for controlling the release of an insect juvenile, hormone from chemical degradation by incorporating the hormone into gel discs containing water soluble sodium alginate, a calcium salt for gelatinization, a solubilizing agent, and a biocide.

The present invention is a controlled or sustained release tablet comprising an active ingredient and a microbially produced alginate-type polysaccharide ("bioalgin"), which is effective for controlling release of the active ingredient in the stomach or the intestine.

SUMMARY OF THE INVENTION

The invention relates to pharmaceutical composition tablets comprising a therapeutically effective amount of an active ingredient to be released in a stomach or intestine and an amount of microbially produced alginate-type polysaccharide between about 5–50% wt. of the tablet. Preferably, the amount of microbially produced alginate-type polysaccharide is between about 10–30% wt. of the tablet. The amount of active ingredient is preferably between about 1–40% wt. of the tablet.

The invention also includes pharmaceutical composition tablets as described above with the exception that some of the microbially produced alginate-type polysaccharide or derivative thereof is replaced with algal alginate. Compositions comprising both bioalgin and algal alginates comprise at least 10% bioalgin and no more than 20% algal alginate.

The invention is also a method for administering a pharmaceutical active ingredient to a patient which comprises preparing a tablet comprising a therapeutically effective amount of the active ingredient to be released in a stomach or intestine and an amount of microbially produced alginate-type polysaccharide between about 5–50% wt. of the tablet, and orally administering the tablet to the patient to deliver the tablet to the stomach or intestine. Preferably, the amount of microbially produced alginate-type polysaccharide is between about 10–30% wt. of the tablet. The amount of active ingredient is preferably between about 1–40% wt. of the tablet.

FIG. 2 shows the dramatic effect of replacing algal alginate with microbially produced alginate-type polysaccharide in a controlled release tablet. After 2 hours, tablets with 20% algal alginate released more than 80% of the tablet formulation active ingredient, while tablets with 20% microbially produced alginate-type polysaccharide released less than 30%. Even tablets with 10% microbially produced alginate-type polysaccharide showed enhanced delayed release (only about 40% of the tablet formulation active ingredient was released after 2 hours) as compared to tablets with 20% algal alginate.

DETAILED DESCRIPTION OF THE INVENTION

Figure 1:
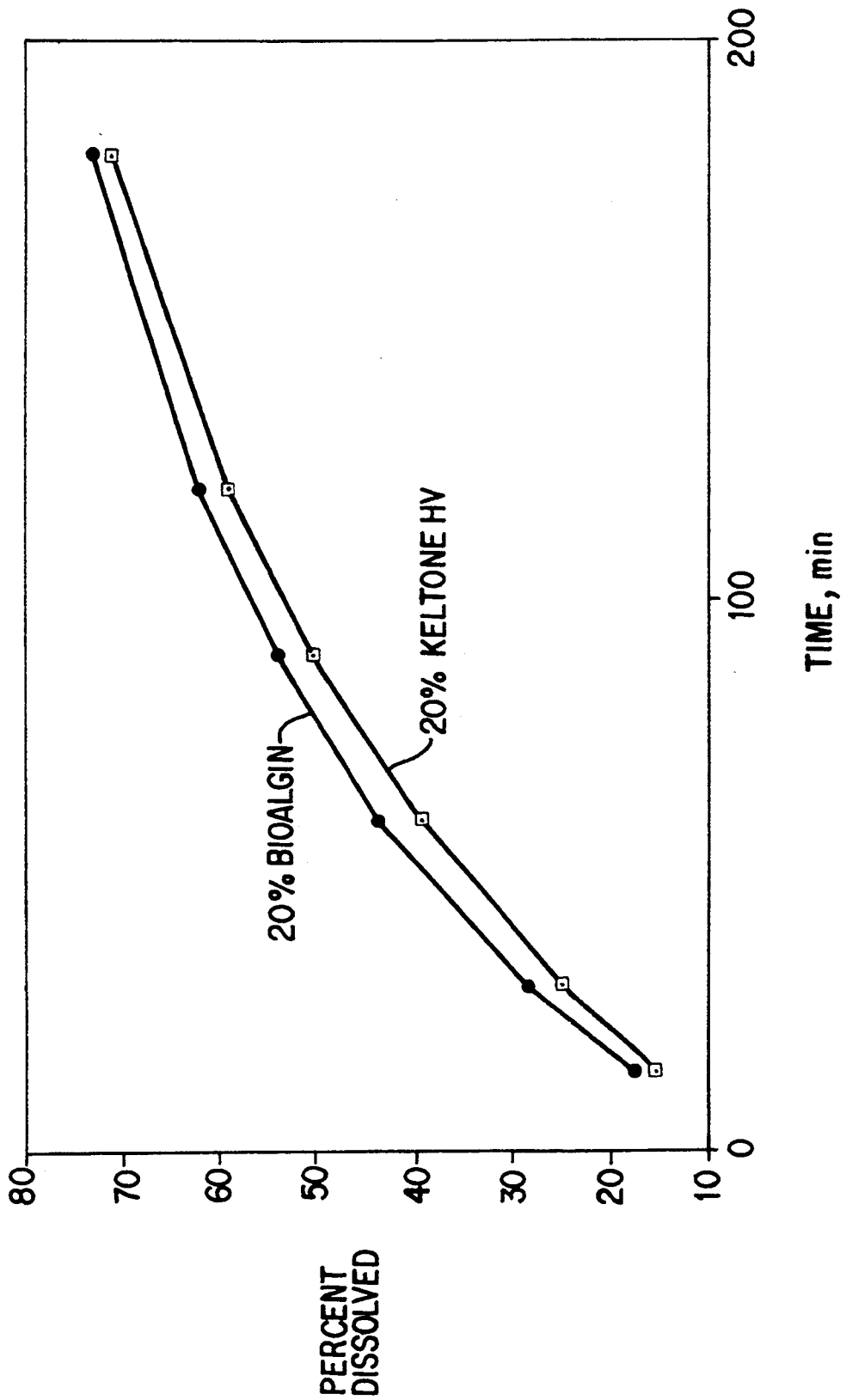
FIG. 1 shows release into simulated gastric fluid of theophylline from tablets containing either algal alginate or bioalgin.

The term "bioalgin" refers to microbially produced polysaccharides, and derivatives thereof, produced by both Pseudomonas and Azotobacter strains as described in Jarman et al., U.S. Pat. No. 4,235,966. These polysaccharides are alginates consisting of a partially acetylated variable block copolymer of D-mannuronic and L-guluronic acid residues. Jarman et al. state that the polysaccharide produced is similar to that produced from seaweed except that the molecule is partially acetylated.

Biolalgin derivatives include deacetylated microbially produced polysaccharides subjected to alkaline conditions followed by precipitation, e.g. high pH using sodium carbonate or sodium hydroxide at elevated temperatures.

The term "algal" alginate refers to naturally derived alginic acid and salts thereof. Naturally derived alginic acid, derived primarily from kelp, is a commercially available product, e.g., KELACID® (Kelco Div., Merck & Co., Inc.). The salts include appropriate metal salts, e.g. alkali metal, alkaline earth metal, ammonium salts, and organic derivatives, e.g. alkylene gylcol, propylene glycol and the like. The salts are preferably water soluble. The preferred salts are sodium, potassium, magnesium, ammonium and propylene glycol algal alginate. KELTONE HV® is a high viscosity sodium algal alginate available from Kelco Div., Merck & Co., Inc.

Among the active therapeutic agents which are useful in the present invention are sedatives, vitamins, anti-inflammatory agents, vasodilators, stimulants, relaxants, suppressants, and many other types of therapeutic agents. Other active ingredients are, for example, isosorbide dinitrate or mononitrate (employed in the treatment of angina pectoris), theophylline (employed in the treatment of asthma), nitroglycerin, ibuprofen, and acetaminophen.

In preparing the pharmaceutical compositions of the invention, the desired ratio of active ingredient and tablet forming material is introduced into a mixing vessel. Ingredients which may be introduced into the mixing vessel are, for example, fillers, e.g. lactose, drying agents, lubricants, e.g. magnesium stearate, coloring agents, starch, and other materials well known in the art. Thereafter the base mixture is typically agitated and mixed for from 20 to 40 minutes and usually from 30 to 40 minutes to achieve uniformity of the active ingredients with the base mixture. Mixing equipment may be, for example, a Day mixer or a Pony mixer.

After a uniform mixture has been obtained, it is transferred to a shaping and compressing step is performed as is well known in the art. The equipment used for such steps may be, for example, Stokes or Colton rotary machines or other tablet compressing machines.

A typical procedure for combining the various ingredients and making the various tablets in the Examples below, is as follows:

The base ingredients are mixed for about 20 minutes in a Day powder mixer or a Pony mixer. Active ingredient is added to the base mixture and the mixture is again mixed for about 30 minutes, adding lubricants. The ingredients are conventionally compressed into tablets of varying shape, including capsule and round shape. For example, round tablets having ⅜" punch size and 15–20 kg hardness are prepared. In the examples presented below, the potency of the tablet is 100 mg active ingredient per 400 mg tablet.

EXAMPLE 1

Following the general procedures described above, controlled release tablets containing the following ingredients were prepared:

| Ingredients | Formulation (wt. %) | | |
|---|---|---|---|
| | A | B | C |
| KELTONE HV® | 20 | — | — |
| Theophylline | 25 | 25 | 25 |
| Lactose | 54 | 54 | 64 |
| Magnesium Stearate | 1 | 1 | 1 |
| Bioalgin | — | 20 | 10 |

Ingredient amounts are shown in dry weight.

The accompanying figures show a comparison of bioalgin and algal alginate (KELTONE HV®, available from Kelco, a Division of Merck & Co., Inc.) in a controlled release tablet formulation. The tablets were 400 mg total weight and contained 100 mg of the drug theophylline. The tablets also contained lactose as a filler and 1% magnesium stearate as a lubricant. The powders were dry blended and tablets were produced by direct compression on a Stokes laboratory model tablet press. Dissolution rates were determined with a Milton Roy Tablet Dissolution System wherein the concentration of the drug was determined spectrophotometrically.

FIG. 1 shows a comparison of tablets containing 20% of each type of alginate in simulated gastric fluid at pH 1.2. Simulated gastric fluid includes 0.1N HCl and 0.2% NaCl. Very little difference is observed between the two.

Figure 2:
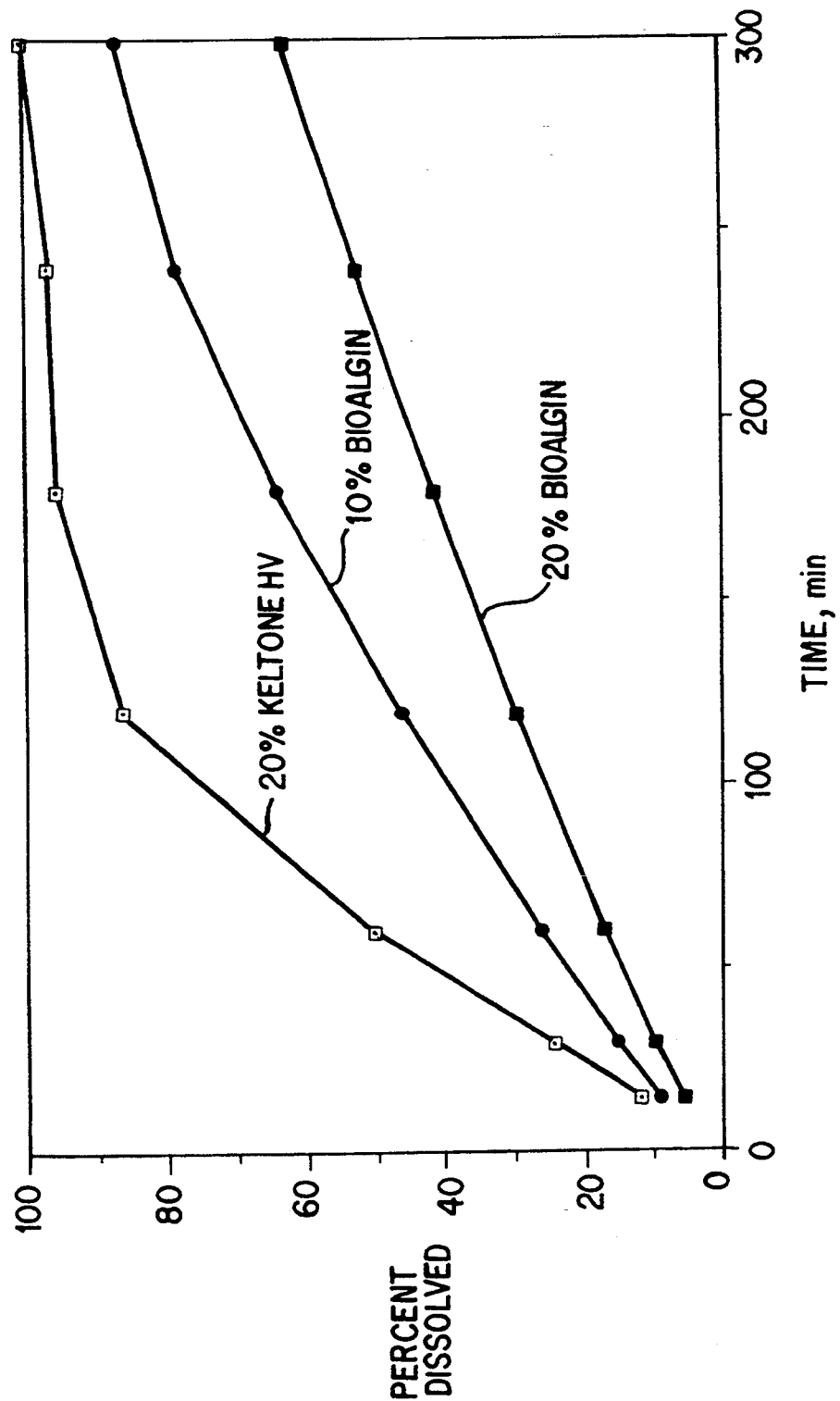
FIG. 2 shows release into simulated intestinal fluid of theophylline from tablets containing either algal alginate or bioalgin.

In FIG. 2, the dissolution rate in simulated intestinal fluid (pH 7.5 phosphate buffer without enzyme prepared as described in USP XXI p. 124 as "Test Solutions") is shown. The dissolution rate is slower at even half the concentration of the algal alginate, and much slower at equal concentrations. After three hours, tablets containing KELTONE HV® were almost completely dissolved, while those containing bioalgin retained their integrity even after six hours.

What is claimed is:

1. A pharmaceutical composition tablet comprising a therapeutically effective amount of an active ingredient to be released in a stomach or intestine and an alginate, the alginate consisting essentially of a partially acetylated variable block copolymer alginate of D-mannuronic and L-guluronic acid produced by Pseudomonas or Azotobacter strains, in an amount between about 5–50% wt. of the tablet.

2. The composition of claim 1 wherein the amount of alginate is between about 10–30% wt. of the tablet.

3. The composition of claim 1 wherein the amount of active ingredient is between about 1–40% wt. of the tablet.

4. A method for administering a pharmaceutical active ingredient to a patient which comprises preparing a tablet comprising a therapeutically effective amount of the active ingredient to be released in a stomach or intestine and an alginate, the alginate consisting essentially of a partially acetylated variable block copolymer alginate of D-mannuronic and L-guluronic acid produced by Pseudomonas or Azotobacter strains, in an amount between about 5–50% wt. of the tablet, and orally administering the tablet to the patient to deliver the tablet to the stomach or intestine.

5. The method of claim 4 wherein the amount of alginate is between about 10–30% wt. of the tablet.

6. The method of claim 4 wherein the amount of active ingredient is between about 1–40% wt. of the tablet.

* * * * *